US00PP27526P2

(12) United States Plant Patent
Hurd

(10) Patent No.: US PP27,526 P2
(45) Date of Patent: Jan. 3, 2017

(54) ***PEROVSKIA* PLANT NAMED 'ROCKETMAN'**

(50) Latin Name: ***Perovskia atriplicifolia* (Benth.)**
Varietal Denomination: Rocketman

(71) Applicant: Kevin A. Hurd, Austin, TX (US)

(72) Inventor: Kevin A. Hurd, Austin, TX (US)

(73) Assignee: Walters Gardens, Inc., Zeeland, MI (US)

( * ) Notice: Subject to any disclaimer, the term of this patent is extended or adjusted under 35 U.S.C. 154(b) by 75 days.

(21) Appl. No.: 14/545,523

(22) Filed: May 15, 2015

(51) Int. Cl.
*A01H 5/02* (2006.01)

(52) U.S. Cl.
USPC ..... Plt./263.1

(58) Field of Classification Search
USPC ..... Plt./263.1
See application file for complete search history.

*Primary Examiner* — Anne Grunberg

(57) ABSTRACT

The new and distinct cultivar of ornamental, hardy, Russian Sage, *Perovskia* 'Rocketman' with short compact habit of strong erect stems, extended flowering season of large, densely-arranged, lavender-blue flowers and silvery green serrate foliage.

1 Drawing Sheet

Botanical classification: *Perovskia atriplicifolia* (Benth.).
Variety denomination: 'Rocketman'.

BACKGROUND OF THE INVENTION

The present invention relates to a new and distinct plant of Russian sage, botanically known as *Perovskia atriplicifolia* 'Rocketman' and will be referred to hereinafter also by its cultivar name 'Rocketman' and the new plant. The new plant cultivar of *Perovskia* is a hardy herbaceous perennial grown for landscape use.

*Perovskia* 'Rocketman' is from the selection of seed from *Perovskia atriplicifolia* 'Little Spire' collected by the inventor Kevin A. Hurd in the summer of 2008 at a nursery in Zeeland, Mich. All subsequent evaluations were performed in a full-sun trial garden at the same nursery with loamy sand soil and irrigation and fertilizer as required. The plant was of a single seedling initially selected for further evaluation during the summer of 2008 and given the breeder designation "08-01-02." The plant was propagated by stem cuttings at the same nursery in Zeeland, Mich. and the original plant and the cuttings evaluated over the next four years until final approval for introduction in the summer of 2013. The resultant asexually propagated cuttings have been stable and identical to the original plant in successive asexual propagations.

*Perovskia atriplicifolia* 'Rocketman' has not been advertised or sold more than one year prior to filing this application, and all disclosures have come either directly or indirectly from the inventor.

SUMMARY OF THE INVENTION

*Perovskia atriplicifolia* 'Rocketman' differs from its parent as well as all other hardy Russian sage known to the inventor in a combination of traits. The following characteristics in combination distinguish 'Rocketman' from all other *Perovskia* plants known to the inventor:

1. Short, compact and upright habit with erect strong stems;

2. Extended flowering season of large, densely-arranged, lavender-blue flowers;
3. Silvery-green, oblanceolate to elliptic, serrated foliage.

The nearest comparison plants are Perovskia 'LISSLITT' U.S. Plant Pat. No. 20,845, 'Blue Spire' (not patented), and the parent 'Little Spire' U.S. Plant Pat. No. 11,643. Compared to cultivar 'LISSLITT', *Perovskia* 'Rocketman' has flowers with longer styles and shorter filaments, petals with purple coloring deeper into the flower throat, calyxes with less pubescence, stiffer and more upright habit with no flopping, and serrate oblanceolate to elliptic foliage instead of highly dissected. Compared to 'Blue Spire' the new plant is much shorter and more compact in habit, has larger and more densely arranged flowers and the foliage is oblanceolate and serrate rather than dissected. Compared to 'Little Spire' the new plant is slightly shorter and less dense in flower habit and the leaves are broader with more acute apex and base and the mature habit is more upright and does not tend to arch and splay open later in the season.

Compared to both 'Filagran' (not patented) and 'Longin' (not patented) 'Rocketman' is more dense in flower and the foliage is not as dissected. The new plant is also significantly shorter in habit than 'Longin'. 'Rocketman' also has larger calyxes than all the above five comparison plants and produces a denser flower effect.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, source and direction may cause the appearance of minor variation in color. The plant used in the photograph is a three-year old plant grown in full sun field in loamy sand soil in trial gardens of a nursery in Zeeland, Mich.

DETAILED BOTANICAL DESCRIPTION

Figure 1:
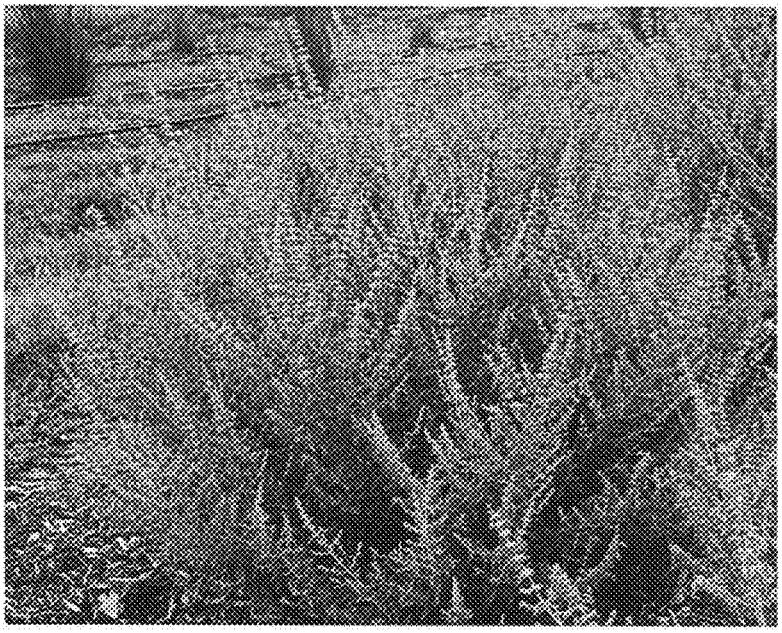
FIG. 1 shows 'Rocketman' in the landscape.
Figure 2:
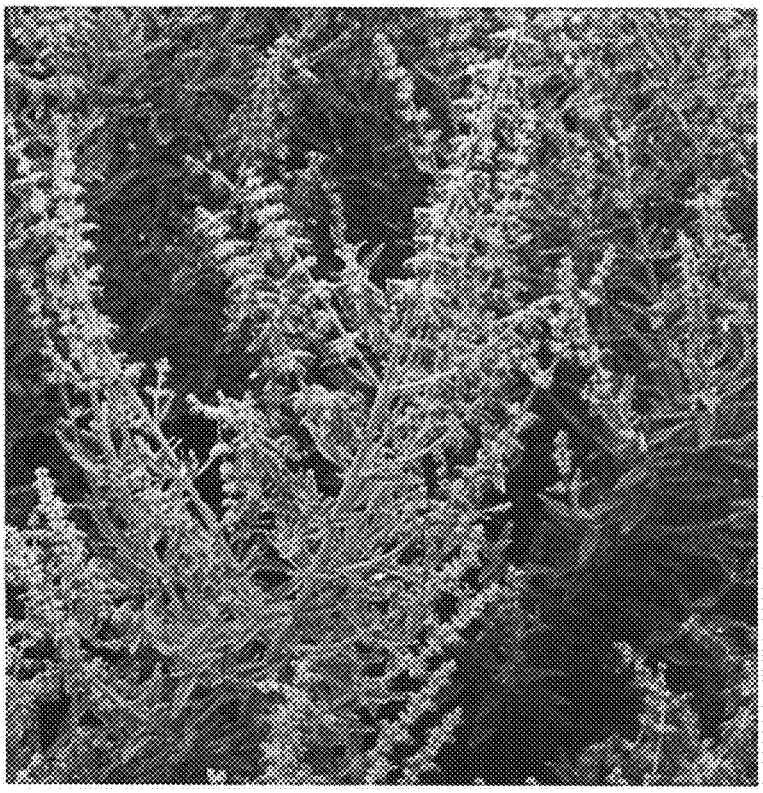
FIG. 2 shows a close-up of the flower stems of 'Rocketman'.

The following is a detailed description of *Perovskia atripicifolia* 'Rocketman' as observed and compared to other cultivars for five years in trial gardens and production fields at a nursery in Zeeland, Mich. The following description is of a three-year old plant of *Perovskia atripicifolia* 'Rocketman' in a full-sun display garden in Zeeland, Mich. with limited supplemental fertilizer and irrigation as needed. The new plant has not been observed under all possible environments, and the phenotype may vary slightly with different environmental conditions, such as temperature, light, fertility, moisture and maturity levels, but without any change in the genotype. The color descriptions are in accordance with The 2001 edition of The R.H.S. Colour Chart of The Royal Horticultural Society, London, England, except where common dictionary color terms are used.

Plant habit: Upright and dense shape; oppositely branched; deciduous, semi-woody sub-shrub usually dying to the ground in most Michigan winters and re-sprouting with new stems from the base each spring; about 20 stems per plant.

Plant size: With high irrigation reaches a maximum of about 90 cm in height, average stem height of about 70 cm, and about 130 cm in width about 50 cm above soil; with lower irrigation maximum height of about 70 cm and width of about 90 cm, but very upright in either environment.

Root description: Fibrous.

Propagation: Stem cuttings; root initiation occurs in 14 to 21 days at a temperature of 20° C.

Growth rate: Moderately vigorous.

Stem description: Quadangular; opposite; lanulose; older stems becoming woody at base; average about 70 cm long and about 9.0 mm across near base; about 20 to 30 branches per stem; with herbal fragrance.

Stem color: Nearest RHS 189D in upper or distal region closer to flowers, and between RHS 191B and RHS 191C in lower or proximal region.

Internode length: Average 2.2 cm.

Internode color: Same as surrounding stem.

Branches: Quadangular; opposite; lanulose; about 45° angle from stem; lower branches about 42.0 cm long and about 2.5 mm diameter, decreasing distally to upper branches about 6.0 cm long and about 1.0 mm diameter.

Branch color: Same as nearby stem.

Foliage description: Opposite, lanceolate to elliptic, acute apex and cuneate base; distal one-half margin serrate, proximal one-half entire; finely pubescent on abaxial and adaxial surfaces; about 3.5 cm long and about 10.0 mm wide; with herbal fragrance.

Leaf color: Emerging leaves nearest RHS 192A both surfaces; mature leaves abaxial surface between RHS 138A and RHS 138B and adaxial surface nearest RHS N138B.

Leaf venation: Reticulate.

Vein color: Adaxial veins nearest RHS N138A; abaxial main vein nearest RHS 192D with tinting of between RHS N186C and RHS N187C and secondary veins nearest RHS 138A.

Petiole: Flattened abaxial to adaxial, slightly concavo-convex; average about 3.0 mm long and about 1.5 mm across at stem.

Petiole color: Adaxial surface nearest RHS N138A; abaxial nearest RHS 192D with tinting of between RHS N186C and RHS N187C.

Inflorescence: Main stems vertical, branched verticillate panicle; about 14.5 cm tall above last branch and about 2.5 cm across; including branches of single stem total inflorescence portion average about 60.0 cm tall and about 36.0 cm wide.

Flower buds about one day prior to opening: About 8.0 mm long and about 2.5 mm wide; long ovoid; calyx with dense long pubescence about 1.0 mm long.

Bud color: Calyx hairs between RHS 85B and RHS 85A; calyx nearest RHS 86A; extended petal portion between RHS 90A and RHS 90B.

Flowers: Bilabiate with upper and lower lip, zygomorphic; about 14.0 mm long and about 8.0 mm wide; petals fused into tube in the proximal 8.5 mm, face opening to nearly flat; up to 15 flowers per verticil and over 600 per main stem.

Fragrance: Slight herbal.

Corolla: Glabrous; bilabitate; upper lip four-lobed each lobe about 2.0 mm across and about 2.0 mm long; lower lip entire with rounded apex curled underneath on edges, about 4.6 mm long and about 4.5 mm wide at base; opening to nearly a flat face; upper and lower lobe apices rounded; base fused into tube; tube about 8.5 mm in length and about 2.0 mm in width.

Corolla color: Adaxial distal portion between RHS N88A and RHS N88B with proximal fused portion lighter than RHS 91D and mid-portion showing veining of nearest RHS 93A; abaxial distal portion nearest RHS 93B with the basal one third inside corolla lighter than RHS 91D.

Gynoecium: One pistil.

*Style*.—About 12.0 mm long and less than about 0.5 mm wide; color nearest RHS 90B distally and lightening to lighter than RHS 91D toward base.

*Stigma*.—Splitting into two and curling around in the terminal 1.0 mm; color nearest RHS 93A.

Androecium: Four, two fertile and two sterile; outer pair sterile and inner pair fertile; stamens adnate to corolla.

*Filaments* (*fertile pair*).—Curled; about 5.0 mm in length and less than about 0.5 mm in width; color nearest RHS 85D.

*Filaments* (*sterile pair*).—Without filament.

*Anther*.—Fertile pair elliptic; about 1.0 mm long and 0.5 mm across, versatile; color nearest RHS N92B; sterile pair flattened ovoid, about 0.5 mm long; color nearest RHS 155D.

*Pollen*.—Sparse in quantity; color lighter than RHS 155D.

Calyx: Tubular campanulate; about 5.0 mm long and about 2.5 mm across; made up of five sepals fused at base in the proximal 4.5 mm with apical 1.5 mm separate; entire, apex acute; outside densely pubescent and glandular at surface, inside glabrous; persistent for weeks after flower abscission and drop.

Calyx color: Outside underneath color at flowering nearest RHS 86A and hairs between RHS 85B or RHS 85A, inside color is nearest RHS 85B with veins nearest RHS 86A.

Seed: Ovoid to spatulate in outline; about 2.0 mm long and about 1.0 mm diameter; color nearest RHS 200D.

Hardiness to at least U.S.D.A. zones 4 to 9: The new plant is very resistant to drought once established and even tolerant of clay soils if good drainage is provided.

Pest and disease resistance: Like other Russian sage, 'Rocketman' is resistant to deer browsing. No susceptibility or resistance to diseases or pests has been observed except that which is common to *Perovskia*.

I claim:

1. A new and distinct cultivar of hardy Russian sage plant, *Perovskia* 'Rocketman', as herein described and illustrated, with short, compact habit of strong erect stems, extended flowering season of large, densely-arranged, lavender-blue flowers and silvery green serrate foliage, suitable as a potted plant, as fresh or dried arrangements, for the garden as an accent or en mass.

* * * * *